United States Patent
Dai et al.

(10) Patent No.: US 10,566,652 B2
(45) Date of Patent: Feb. 18, 2020

(54) LITHIUM METAL BATTERY WITH HYBRID ELECTROLYTE SYSTEM

(71) Applicant: GM Global Technology Operations LLC, Detroit, MI (US)

(72) Inventors: Fang Dai, Troy, MI (US); Li Yang, Troy, MI (US); Thomas A. Yersak, Ferndale, MI (US); James R. Salvador, Royal Oak, MI (US); Mei Cai, Bloomfield Hills, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 155 days.

(21) Appl. No.: 15/677,760

(22) Filed: Aug. 15, 2017

(65) Prior Publication Data
US 2019/0058210 A1    Feb. 21, 2019

(51) Int. Cl.
*H01M 10/056* (2010.01)
*H01M 10/0525* (2010.01)
(Continued)

(52) U.S. Cl.
CPC ......... *H01M 10/056* (2013.01); *H01M 4/131* (2013.01); *H01M 4/382* (2013.01);
(Continued)

(58) Field of Classification Search
CPC .................................................. H01M 10/056
(Continued)

(56) References Cited

U.S. PATENT DOCUMENTS

| 8,974,946 B2 | 3/2015 | Cai et al. |
| 9,160,036 B2 | 10/2015 | Yang et al. |

(Continued)

FOREIGN PATENT DOCUMENTS

| CN | 106159159 A | 11/2016 |
| CN | 109411811 A | 3/2019 |
| DE | 102018119757 A1 | 2/2019 |

OTHER PUBLICATIONS

Li Yang et al.; U.S. Appl. No. 15/295,600, filed Oct. 17, 2016 entitled "Three-Electrode Test Cell"; 33 pages.
(Continued)

*Primary Examiner* — Sean P Cullen
(74) *Attorney, Agent, or Firm* — Harness, Dickey & Pierce, P.L.C.

(57) ABSTRACT

An electrochemical cell includes a negative electrode that contains lithium and an electrolyte system. In one variation, the electrolyte system includes a first liquid electrolyte, a solid-dendrite-blocking layer, and an interface layer. The solid dendrite-blocking layer is ionically conducting and electrically insulating. The dendrite-blocking layer includes a first component and a distinct second component. The dendrite-blocking layer has a shear modulus of greater than or equal to about 7.5 GPa at 23° C. The interface layer is configured to interface with a negative electrode including lithium metal on a first side and the dendrite blocking layer on a second opposite side. The interface layer includes a second liquid electrolyte, a gel polymer electrolyte, or a solid-state electrolyte. The dendrite-blocking layer is disposed between the first liquid electrolyte and the interface layer.

20 Claims, 5 Drawing Sheets

(51) Int. Cl.

| | | |
|---|---|---|
| *H01M 4/131* | (2010.01) | |
| *H01M 4/38* | (2006.01) | |
| *C07C 69/96* | (2006.01) | |
| *C08G 65/08* | (2006.01) | |

(52) U.S. Cl.
CPC ......... *H01M 10/0525* (2013.01); *C07C 69/96* (2013.01); *C08G 65/08* (2013.01)

(58) Field of Classification Search
USPC ....................................................... 429/188
See application file for complete search history.

(56) References Cited

U.S. PATENT DOCUMENTS

| | | | |
|---|---|---|---|
| 9,252,411 B2 | 2/2016 | Abd Elhamid et al. | |
| 9,373,829 B2 | 6/2016 | Xiao et al. | |
| 9,647,254 B2 | 5/2017 | Dadheech et al. | |
| 9,742,028 B2 | 8/2017 | Zhou et al. | |
| 2008/0268327 A1* | 10/2008 | Gordon | H01M 2/1646 429/50 |
| 2009/0136830 A1* | 5/2009 | Gordon | H01M 10/052 429/50 |
| 2012/0251869 A1* | 10/2012 | Lee | H01M 2/1633 429/144 |
| 2014/0170465 A1 | 6/2014 | Visco et al. | |
| 2015/0056387 A1 | 2/2015 | Dadheech et al. | |
| 2015/0056493 A1 | 2/2015 | Dadheech et al. | |
| 2015/0236324 A1 | 8/2015 | Xiao et al. | |
| 2015/0349307 A1 | 12/2015 | Dadheech et al. | |
| 2016/0020491 A1 | 1/2016 | Dai et al. | |
| 2016/0064770 A1* | 3/2016 | Lee | H01M 4/382 429/303 |
| 2016/0141598 A1 | 5/2016 | Dai et al. | |
| 2016/0172665 A1 | 6/2016 | Zhou et al. | |
| 2016/0172681 A1 | 6/2016 | Yang et al. | |
| 2016/0172706 A1 | 6/2016 | Xiao et al. | |
| 2016/0172710 A1 | 6/2016 | Liu et al. | |
| 2016/0181658 A1* | 6/2016 | Kim | H01M 10/052 429/200 |
| 2016/0218342 A1 | 7/2016 | Xiao et al. | |
| 2016/0254567 A1 | 9/2016 | Cai et al. | |
| 2017/0162859 A1 | 6/2017 | Yang et al. | |
| 2017/0214079 A1 | 7/2017 | Dai et al. | |
| 2017/0222210 A1 | 8/2017 | Xiao | |
| 2017/0271678 A1 | 9/2017 | Yang et al. | |
| 2017/0288230 A1 | 10/2017 | Yang et al. | |
| 2017/0288281 A1* | 10/2017 | Chiang | H01M 2/145 |
| 2017/0338490 A1 | 11/2017 | Xiao et al. | |
| 2018/0048022 A1 | 2/2018 | Yang et al. | |
| 2018/0062206 A1 | 3/2018 | Yang et al. | |
| 2018/0108952 A1 | 4/2018 | Yang et al. | |
| 2018/0309165 A1 | 10/2018 | Yersak et al. | |
| 2018/0309166 A1 | 10/2018 | Yersak et al. | |
| 2018/0375148 A1 | 12/2018 | Yersak et al. | |
| 2019/0044134 A1 | 2/2019 | Liu et al. | |
| 2019/0058211 A1 | 2/2019 | Yang et al. | |
| 2019/0067675 A1 | 2/2019 | Xiao | |
| 2019/0067744 A1 | 2/2019 | Xiao et al. | |
| 2019/0089006 A1 | 3/2019 | Yang et al. | |

OTHER PUBLICATIONS

Fang Liu et al.; U.S. Appl. No. 15/666,170, filed Aug. 1, 2017 entitled "Conformal Coating of Lithium Anode via Vapor Deposition for Rechargeable Lithium Ion Batteries"; 52 pages.

Li Yang et al.; U.S. Appl. No. 15/677,249, filed Aug. 15, 2017 entitled "Ether-Based Electrolyte System Improving or Supporting Anodic Stability of Electrochemical Cells Having Lithium-Containing Anodes"; 44 pages.

Xingcheng Xiao; U.S. Appl. No. 15/692,107, filed Aug. 31, 2017 entitled "Methods of Applying Self-Forming Artificial Solid Electrolyte Interface (Sei) Layer to Stabilize Cycle Stability of Electrodes in Lithium Batteries"; 45 pages.

Li Yang et al.; U.S. Appl. No. 15/710,326, filed Sep. 20, 2017 entitled "Hybrid Metal-Organic Framework Separators for Electrochemical Cells"; 46 pages.

H. Zhou, Y. Wang, H. Li, and P. He, "The development of a new type of rechargeable batteries based on hybrid electrolytes," ChemSusChem, vol. 3, No. 9, pp. 1009-1019, 2010.

J. Christensen, P. Albertus, R. S. Sanchez-Carrera, T. Lohmann, B. Kozinsky, R. Liedtke, J. Ahmed, and A. Kojic, "A Critical Review of Li/Air Batteries," J. Electrochem. Soc., vol. 159, No. 2, p. R1, 2012.

L. Wang, Y. Wang, and Y. Xia, "A high performance lithium-ion sulfur battery based on a $Li_2S$ cathode using a dual-phase electrolyte," Energy Environ. Sci., vol. 8, No. 5, pp. 1551-1558, 2015.

Q. Wang, Z. Wen, J. Jin, J. Guo, X. Huang, J. Yang, and C. Chen, "A gel-ceramic multi-layer electrolyte for long-life lithium sulfur batteries," Chem. Commun., vol. 52, No. 8, pp. 1637-1640, 2016.

W. Zhou, S. Wang, Y. Li, S. Xin, A. Manthiram, and J. B. Goodenough, "Plating a Dendrite-Free Lithium Anode with a Polymer/ Ceramic/ Polymer Sandwich Electrolyte," J. Am. Chem. Soc., vol. 138, pp. 9385-9388, 2016.

X. Yu, Z. Bi, F. Zhao, and A. Manthiram, "Hybrid Lithium-Sulfur Batteries with a Solid Electrolyte Membrane and Lithium Polysulfide Catholyte," ACS Appl. Mater. Interfaces, vol. 7, pp. 16625-16631, 2015.

X. Yu, Z. Bi, F. Zhao, and A. Manthiram, "Polysulfide-Shuttle Control in Lithium-Sulfur Batteries with a Chemically / Electrochemically Compatible NaSICON-Type Solid Electrolyte," Adv. Energy Mater., p. 1601392, 2016.

Y. Li, B. Xu, H. Xu, H. Duan, X. Lü, S. Xin, W. Zhou, L. Xue, G. Fu, and A. Manthiram, "Hybrid Polymer/Garnet Electrolyte with a Small Interfacial Resistance for Lithium-Ion Batteries," Angew. Chemie, vol. 129, No. 3, pp. 771-774, 2017.

Y. Wang and H. Zhou, "A lithium-air battery with a potential to continuously reduce $O_2$ from air for delivering energy," J. Power Sources, vol. 195, No. 1, pp. 358-361, 2010.

Dadheech, Gayatri et al., U.S. Appl. No. 15/953,142, filed Apr. 13, 2018 entitled "Separator for Lithium Metal Based Batteries," 37 pages.

Zhao, Yang et al., "Robust Metallic Lithium Anode Protected by Molecular Layer Deposition Technique"; Small Methods, 2018, DOI: 10.1002/smtd.201700417.

* cited by examiner

LITHIUM METAL BATTERY WITH HYBRID ELECTROLYTE SYSTEM

INTRODUCTION

This section provides background information related to the present disclosure which is not necessarily prior art.

The present disclosure pertains to a lithium metal battery having a hybrid electrolyte system. More specifically, the hybrid electrolyte system includes a liquid electrolyte, an interface layer, and a dendrite-blocking layer disposed between the liquid electrolyte and the interface layer.

High-energy density, electrochemical cells, such as lithium-ion batteries can be used in a variety of consumer products and vehicles, such as Hybrid Electric Vehicles (HEVs) and Electric Vehicles (EVs). Typical lithium-ion and lithium sulfur batteries include a first electrode, a second electrode, an electrolyte material, and a separator. One electrode serves as a positive electrode or cathode and another serves as a negative electrode or anode. A stack of battery cells may be electrically connected to increase overall output. Conventional rechargeable lithium-ion batteries operate by reversibly passing lithium-ions back and forth between the negative electrode and the positive electrode. A separator and an electrolyte may be disposed between the negative and positive electrodes. The electrolyte is suitable for conducting lithium-ions and may be in solid (e.g., solid state diffusion) or liquid form. Lithium-ions move from a cathode (positive electrode) to an anode (negative electrode) during charging of the battery, and in the opposite direction when discharging the battery.

Many different materials may be used to create components for a lithium-ion battery. Common negative electrode materials include lithium insertion materials or alloy host materials, like carbon-based materials, such as lithium-graphite intercalation compounds, or lithium-silicon compounds, lithium-tin alloys, and lithium titanate $Li_{4+x}Ti_5O_{12}$, where $0 \leq x \leq 3$, such as $Li_4Ti_5O_{12}$ (LTO). Where the negative electrode is made of metallic lithium, the electrochemical cell is considered a lithium metal battery or cell. Metallic lithium for use in the negative electrode of a rechargeable battery has various potential advantages, including having the highest theoretical capacity and lowest electrochemical potential. Thus, batteries incorporating lithium metal anodes can have a higher energy density that can potentially double storage capacity, so that the battery may be half the size, but still last the same amount of time as other lithium ion batteries. Thus, lithium metal batteries are one of the most promising candidates for high energy storage systems. However, lithium metal batteries also have potential downsides, including possibly exhibiting unreliable or diminished performance and potential premature electrochemical cell failure.

There are two primary causes for performance degradation with lithium negative electrodes. Side reactions can occur between the lithium metal and species in the adjacent electrolyte disposed between the positive and negative electrodes, which can compromise coulombic efficiency and cycling lifetime of rechargeable lithium batteries. Also, when the lithium metal is recharged, branchlike or fiber-like metal structures, called dendrites, can grow on the negative electrode. The metal dendrites may form sharp protrusions that potentially puncture the separator and cause an internal short circuit, which may cause cell self-discharge or cell failure through thermal runaway. Accordingly, it would be desirable to develop reliable, high-performance lithium-containing negative electrode materials for use in high energy electrochemical cells that reduce or suppress both side reactions with the electrolyte and the formation of lithium metal dendrites.

SUMMARY

This section provides a general summary of the disclosure, and is not a comprehensive disclosure of its full scope or all of its features.

In various aspects, the present disclosure provides an electrochemical cell having a negative electrode that contains lithium and an electrolyte system for the electrochemical cell. In one variation, the electrolyte system includes a first liquid electrolyte, a solid-dendrite-blocking layer, and an interface layer. The solid dendrite-blocking layer is ionically conducting and electrically insulating. The dendrite-blocking layer includes a first component and a distinct second component. The dendrite-blocking layer has a shear modulus of greater than or equal to about 7.5 GPa at 23° C. The interface layer is configured to interface with a negative electrode including lithium metal on a first side and the dendrite blocking layer on a second opposite side. The interface layer includes a second liquid electrolyte, a gel polymer electrolyte, or a solid-state electrolyte. The dendrite-blocking layer is disposed between the first liquid electrolyte and the interface layer.

In one aspect, the first component includes a solid state ceramic, glass, or glass-ceramic. The second component includes a polymer.

In one aspect, the polymer includes polyethylene oxide (PEO) and the solid-state ceramic, glass, or glass ceramic is selected from the group consisting of: lithium aluminum titanium phosphate ($Li_{1.3}Al_{0.3}Ti_{1.7}(PO_4)_3$) (LATP)), lithium lanthanum titanate ($Li_{0.67-x}La_{3x}TiO_3$) (LLTO)), lithium lanthanum zirconium oxide ($Li_7La_3Zr_2O_{12}$) (LLZO)), lithium phosphorous sulfide ($70Li_2S-30P_2S_5$) (LPS), and combinations thereof.

In one aspect, the dendrite-blocking layer has a composite structure including the first component and the second component.

In one aspect, the dendrite-blocking layer has a laminate structure including one or more layers of the first component and one or more layers of the second component.

In one aspect, the dendrite-blocking layer is impermeable to the first liquid electrolyte.

In one aspect, the electrolyte system further includes further including a polymeric membrane disposed between the first liquid electrolyte and the dendrite-blocking layer.

In another variation, the present disclosure provides an electrochemical cell including a positive electrode, a negative electrode, and an electrolyte system. The negative electrode includes lithium. The electrolyte system includes a solid dendrite-blocking layer and a first liquid electrolyte. The dendrite-blocking layer is disposed between the positive electrode and the negative electrode. The first liquid electrolyte is disposed between the positive electrode and the dendrite-blocking layer. The dendrite-blocking layer has a shear modulus of greater than or equal to about 7.5 GPa at 23° C., is electrically insulating, and includes a first component and a second distinct component.

In one aspect, first component includes a solid-state ceramic, glass, or glass-ceramic and the second component includes a polymer.

In one aspect, the polymer includes polyethylene oxide (PEO) and the solid-state ceramic, glass, or glass-ceramic is selected from the group consisting of: lithium aluminum titanium phosphate ($Li_{1.3}Al_{0.3}Ti_{1.7}(PO_4)_3$) (LATP)), lithium lanthanum titanate ($Li_{0.67-x}La_{3x}TiO_3$) (LLTO)), lithium lanthanum zirconium oxide ($Li_7La_3Zr_2O_{12}$) (LLZO)), lithium phosphorous sulfide ($70Li_2S\text{-}30P_2S_5$) (LPS), and combinations thereof.

In one aspect, the electrolyte system further includes an interface layer. The interface layer is disposed between the dendrite-blocking layer and the negative electrode. The interface layer is configured to interface with the dendrite-blocking layer and the negative electrode. The interface layer includes a second liquid electrolyte, a polymer gel electrolyte, or a solid-state electrolyte.

In one aspect, the interface layer includes an ether-based electrolyte.

In one aspect, the dendrite-blocking layer has a composite structure including the first component and the second component.

In one aspect, the dendrite-blocking layer has a laminate structure including one or more layers of the first component and one or more layers of the second component.

In one aspect, the first liquid electrolyte is in direct contact with the dendrite-blocking layer.

In one aspect, the electrolyte system further includes a polymeric membrane. The polymeric membrane is disposed between the first liquid electrolyte and the dendrite-blocking layer.

In one aspect, the positive electrode includes a metal oxide. The metal oxide is selected from the group consisting of: lithium cobalt oxide ($LiCoO_2$) (LCO), lithium manganese oxide ($LiMn_2O_4$) (LMO), lithium nickel manganese spinel ($LiNi_{0.5}Mn_{1.5}O_4$) (LMNO), lithium nickel cobalt aluminum oxide ($LiNiCoAlO_2$) (NCA), lithium nickel cobalt manganese oxide ($LiNiCoMnO_2$) (NMC), lithium iron phosphate ($LiFePO_4$) (LFP), and combinations thereof.

In one aspect, the first liquid electrolyte is a carbonate-based electrolyte. The carbonate-based electrolyte is selected from the group consisting of: ethylene carbonate (EC), propylene carbonate (PC), butylene carbonate (BC), fluoroethylene carbonate (FEC), dimethyl carbonate (DMC), diethyl carbonate (DEC), ethylmethylcarbonate (EMC), and combinations thereof.

In still another variation, the present disclosure provides an electrochemical cell including a positive electrode, a negative electrode, and an electrolyte system. The positive electrode includes a metal oxide. The negative electrode includes lithium. The electrolyte system includes a solid dendrite-blocking layer, a first electrolyte, and an interface layer. The dendrite-blocking layer is electrically insulating, ionically-conductive, and has a shear modulus of greater than or equal to about 7.5 GPa at 23° C. The dendrite-blocking layer is disposed between the positive electrode and the negative electrode. The first liquid electrolyte is disposed between the positive electrode and the dendrite-blocking layer. The interface layer disposed between the negative electrode and the dendrite-blocking layer. The interface layer is configured to interface with the negative electrode and the dendrite-blocking layer. The interface layer includes a second liquid electrolyte, a gel polymer electrolyte, or a solid-state electrolyte.

In one aspect, the electrolyte system further includes a polymeric membrane disposed between the first liquid electrolyte and the dendrite-blocking layer.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
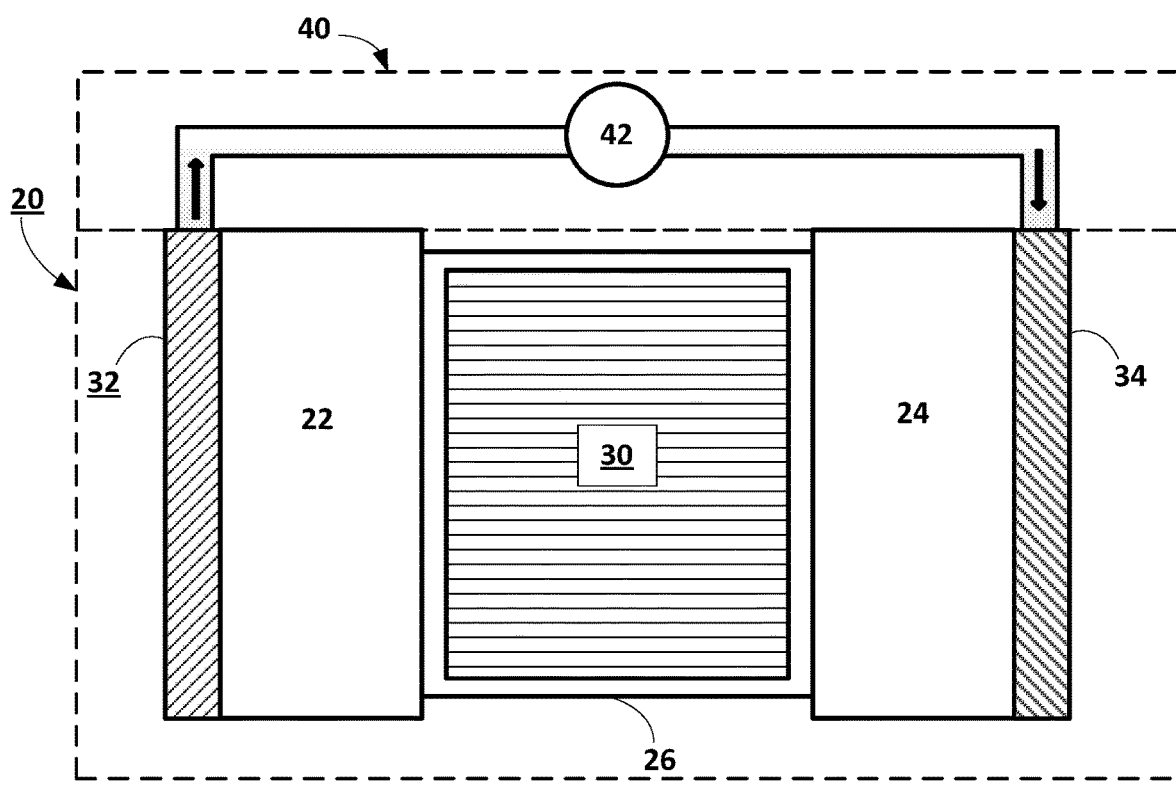
FIG. 1 is a schematic of an exemplary electrochemical battery cell including a lithium-containing negative electrode.

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Any method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

When a component, element, or layer is referred to as being "on," "engaged to," "connected to," or "coupled to" another element or layer, it may be directly on, engaged, connected or coupled to the other component, element, or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various steps, elements, components, regions, layers and/or sections, these steps, elements, components, regions, layers and/or sections should not be limited by these terms, unless otherwise indicated. These terms may be only used to distinguish one step, element, component, region, layer or section from another step, element, component, region, layer or section. Terms such as "first," "second," and other numerical terms when used herein do not imply a sequence or order unless clearly indicated by the context. Thus, a first step, element, component, region, layer or section discussed below could be termed a second step, element, component, region, layer or section without departing from the teachings of the example embodiments.

Spatially or temporally relative terms, such as "before," "after," "inner," "outer," "beneath," "below," "lower," "above," "upper," and the like, may be used herein for ease of description to describe one element or feature's relationship to another element(s) or feature(s) as illustrated in the figures. Spatially or temporally relative terms may be intended to encompass different orientations of the device or system in use or operation in addition to the orientation depicted in the figures.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. For example, "about" may comprise a variation of less than or equal to 5%, optionally less than or equal to 4%, optionally less than or equal to 3%, optionally less than or equal to 2%, optionally less than or equal to 1%, optionally less than or equal to 0.5%, and in certain aspects, optionally less than or equal to 0.1%.

In addition, disclosure of ranges includes disclosure of all values and further divided ranges within the entire range, including endpoints and sub-ranges given for the ranges.

Example embodiments will now be described more fully with reference to the accompanying drawings.

The present technology pertains to improved electrochemical cells, especially lithium-ion or more particularly lithium-metal batteries, which may be used in vehicle applications. However, the present technology may also be used in other electrochemical devices; especially those that comprise lithium, such lithium sulfur batteries, so that the discussion of a lithium-ion battery herein is non-limiting.

An exemplary and schematic illustration of a battery 20 that cycles lithium ion is shown in FIG. 1. Battery 20 includes a negative electrode 22, a positive electrode 24, and a porous separator 26 (e.g., a microporous or nanoporous polymeric separator) disposed between the two electrodes 22, 24. The porous separator 26 includes an electrolyte 30, which may also be present in the negative electrode 22 and positive electrode 24. A negative electrode current collector 32 may be positioned at or near the negative electrode 22 and a positive electrode current collector 34 may be positioned at or near the positive electrode 24. The negative electrode current collector 32 and positive electrode current collector 34 respectively collect and move free electrons to and from an external circuit 40. An interruptible external circuit 40 and load 42 connects the negative electrode 22 (through its current collector 32) and the positive electrode 24 (through its current collector 34).

The porous separator 26 operates as both an electrical insulator and a mechanical support, by being sandwiched between the negative electrode 22 and the positive electrode 24 to prevent physical contact and thus, the occurrence of a short circuit. The porous separator 26, in addition to providing a physical barrier between the two electrodes 22, 24, can provide a minimal resistance path for internal passage of lithium ions (and related anions) during cycling of the lithium ions to facilitate functioning of the battery 20.

The battery 20 can generate an electric current during discharge by way of reversible electrochemical reactions that occur when the external circuit 40 is closed (to connect the negative electrode 22 and the positive electrode 24) when the negative electrode 22 contains a relatively greater quantity of lithium. The chemical potential difference between the positive electrode 24 and the negative electrode 22 drives electrons produced at the negative electrode 22 through the external circuit 40 toward the positive electrode 24. Lithium ions, which are also produced at the negative electrode 22, are concurrently transferred through the electrolyte 30 and porous separator 26 towards the positive electrode 24. The electrons flow through the external circuit 40 and the lithium ions migrate across the porous separator 26 in the electrolyte 30 to the positive electrode 24, where they may be plated, reacted, or intercalated. The electric current passing through the external circuit 18 can be harnessed and directed through the load device 42 until the lithium in the negative electrode 22 is depleted and the capacity of the battery 20 is diminished. While in lithium-ion batteries, lithium intercalates and/or alloys in the electrode active materials, in a lithium sulfur battery, instead of intercalating or alloying, the lithium dissolves from the negative electrode and migrates to the positive electrode where it reacts/plates during discharge, while during charging, lithium plates on the negative electrode.

The battery 20 can be charged or re-energized at any time by connecting an external power source to the battery 20 to reverse the electrochemical reactions that occur during battery discharge. The connection of an external power source to the battery 20 compels the production of electrons and release of lithium ions from the positive electrode 24. The electrons, which flow back towards the negative electrode 22 through the external circuit 40, and the lithium ions, which are carried by the electrolyte 30 across the separator 26 back towards the negative electrode 22, reunite at the negative electrode 22 and replenish it with lithium for consumption during the next battery discharge cycle. As such, each discharge and charge event is considered to be a cycle, where lithium ions are cycled between the positive electrode 24 and negative electrode 22.

The external power source that may be used to charge the battery 20 may vary depending on the size, construction, and particular end-use of the battery 20. Some notable and exemplary external power sources include, but are not limited to, an AC wall outlet and a motor vehicle alternator. In many lithium-ion battery configurations, each of the negative electrode current collector 32, negative electrode 22, the separator 26, positive electrode 24, and positive electrode current collector 34 are prepared as relatively thin layers (for example, from several microns to a millimeter or less in thickness) and assembled in layers connected in electrical parallel arrangement to provide a suitable electrical energy and power package.

Furthermore, the battery 20 can include a variety of other components that while not depicted here are nonetheless known to those of skill in the art. For instance, the battery 20 may include a casing, gaskets, terminal caps, tabs, battery terminals, and any other conventional components or materials that may be situated within the battery 20, including between or around the negative electrode 22, the positive electrode 24, and/or the separator 26, by way of non-limiting example. As noted above, the size and shape of the battery 20 may vary depending on the particular application for which it is designed. Battery-powered vehicles and hand-held consumer electronic devices, for example, are two examples where the battery 20 would most likely be designed to different size, capacity, and power-output specifications. The battery 20 may also be connected in series or parallel with other similar lithium-ion cells or batteries to produce a greater voltage output, energy, and power if it is required by the load device 42.

Accordingly, the battery 20 can generate electric current to a load device 42 that can be operatively connected to the external circuit 40. While the load device 42 may be any number of known electrically-powered devices, a few specific examples of power-consuming load devices include an electric motor for a hybrid vehicle or an all-electric vehicle, a laptop computer, a tablet computer, a cellular phone, and cordless power tools or appliances, by way of non-limiting example. The load device 42 may also be a power-generating apparatus that charges the battery 20 for purposes of storing energy. In certain other variations, the electrochemical cell may be a supercapacitor, such as a lithium-ion based supercapacitor.

With renewed reference to FIG. 1, the porous separator 26 may include, in certain instances, a microporous polymeric separator including a polyolefin, by way of non-limiting example. The polyolefin may be a homopolymer (derived from a single monomer constituent) or a heteropolymer (derived from more than one monomer constituent), which may be either linear or branched. If a heteropolymer is derived from two monomer constituents, the polyolefin may assume any copolymer chain arrangement, including those of a block copolymer or a random copolymer. Similarly, if the polyolefin is a heteropolymer derived from more than two monomer constituents, it may likewise be a block copolymer or a random copolymer. In certain aspects, the polyolefin may be polyethylene (PE), polypropylene (PP), or a blend of PE and PP, or multi-layered structured porous films of PE and/or PP. Commercially available polyolefin porous membranes 26 include CELGARD® 2500 (a monolayer polypropylene separator) and CELGARD® 2320 (a trilayer polypropylene/polyethylene/polypropylene separator) available from Celgard LLC.

When the porous separator 26 is a microporous polymeric separator, it may be a single layer or a multi-layer laminate, which may be fabricated from either a dry or wet process. For example, in one embodiment, a single layer of the polyolefin may form the entire microporous polymer separator 26. In other aspects, the separator 26 may be a fibrous membrane having an abundance of pores extending between the opposing surfaces and may have a thickness of less than a millimeter, for example. As another example, however, multiple discrete layers of similar or dissimilar polyolefins may be assembled to form the microporous polymer separator 26. Furthermore, the porous separator 26 may be mixed with a ceramic material or its surface may be coated in a ceramic material. For example, a ceramic coating may include alumina ($Al_2O_3$), silicon dioxide ($SiO_2$), or combinations thereof. Various conventionally available polymers and commercial products for forming the separator 26 are contemplated, as well as the many manufacturing methods that may be employed to produce such a microporous polymer separator 26.

The positive electrode 24 may be formed from a lithium-based active material that can sufficiently undergo lithium intercalation and deintercalation, alloying and dealloying, or plating and stripping, while functioning as the positive terminal of the battery 20. The positive electrode 24 electroactive materials may include one or more transition metals, such as manganese (Mn), nickel (Ni), cobalt (Co), chromium (Cr), iron (Fe), vanadium (V), and combinations thereof. Two exemplary common classes of known electroactive materials that can be used to form the positive electrode 24 are lithium transition metal oxides with layered structure and lithium transition metal oxides with spinel phase. For example, in certain instances, the positive electrode 24 may include a spinel-type transition metal oxide, like lithium manganese oxide ($Li_{(1+x)}Mn_{(2-x)}O_4$), where x is typically less than 0.15, including $LiMn_2O_4$ (LMO) and lithium manganese nickel oxide $LiMn_{1.5}Ni_{0.5}O_4$ (LMNO). In other instances, the positive electrode 24 may include layered materials like lithium cobalt oxide ($LiCoO_2$), lithium nickel oxide ($LiNiO_2$), a lithium nickel manganese cobalt oxide ($Li(Ni_xMn_yCo_z)O_2$), where $0 \le x \le 1$, $0 \le y \le 1$, $0 \le z \le 1$, and $x+y+z=1$, including $LiMn_{0.33}Ni_{0.33}Co_{0.33}O_2$, a lithium nickel cobalt metal oxide ($LiNi_{(1-x-y)}Co_xM_yO_2$), where $0<x<1$, $0<y<1$ and M may be Al, Mn, or the like. Other known lithium-transition metal compounds such as lithium iron phosphate ($LiFePO_4$) or lithium iron fluorophosphate ($Li_2FePO_4F$) can also be used. In certain aspects, the positive electrode 24 may include an electroactive material that includes manganese, such lithium manganese oxide ($Li_{(1+x)}Mn_{(2-x)}O_4$), a mixed lithium manganese nickel oxide ($LiMn_{(2-x)}Ni_xO_4$), where $0 \le x \le 1$, and/or a lithium manganese nickel cobalt oxide (e.g., $LiMn_{1/3}Ni_{1/3}Co_{1/3}O_2$). In a lithium-sulfur battery, positive electrodes may have elemental sulfur as the active material or a sulfur-containing active material.

In certain variations, such active materials may be intermingled with an optional electrically conductive material and at least one polymeric binder material to structurally fortify the lithium-based active material along with an optional electrically conductive particle distributed therein. For example, the active materials and optional conductive materials may be slurry cast with such binders, like polyvinylidene difluoride (PVdF), ethylene propylene diene monomer (EPDM) rubber, or carboxymethoxyl cellulose (CMC), a nitrile butadiene rubber (NBR), lithium polyacrylate (LiPAA), sodium polyacrylate (NaPAA), sodium alginate, lithium alginate. Electrically conductive materials may include graphite, carbon-based materials, powdered nickel, metal particles, or a conductive polymer. Carbon-based materials may include by way of non-limiting example particles of KETCHEN™ black electrically-conductive carbon black, DENKA™ black electrically-conductive acetylene black, acetylene black, carbon black, and the like. Examples of a conductive polymer include polyaniline, polythiophene, polyacetylene, polypyrrole, and the like. In certain aspects, mixtures of conductive materials may be used. The positive electrode current collector 34 may be formed from aluminum or any other appropriate electrically conductive material known to those of skill in the art.

The negative electrode 22 includes an electroactive material as a lithium host material capable of functioning as a negative terminal of a lithium-ion battery. In various aspects, the electroactive material comprises lithium and may be lithium metal. The negative electrode 22 may thus include the electroactive lithium host material, such as lithium. In certain variations, the negative electrode 22 may optionally include an electrically conductive material, as well as one or more polymeric binder materials to structurally hold the lithium material together. Negative electrodes may comprise greater than or equal to about 50% to less than or equal to about 100% of an electroactive material (e.g., lithium particles or a lithium foil), optionally less than or equal to about 30% of an electrically conductive material, and a balance binder. For example, in one embodiment, the negative electrode 22 may include an active material including lithium metal particles intermingled with a binder material selected from the group consisting of: polyvinylidene difluoride (PVdF), ethylene propylene diene monomer (EPDM) rubber, or carboxymethoxyl cellulose (CMC), a nitrile butadiene rubber (NBR), lithium polyacrylate (Li-PAA), sodium polyacrylate (NaPAA), sodium alginate, lithium alginate, and combinations thereof, by way of non-limiting example. Suitable additional electrically conductive materials may include carbon-based material or a conductive polymer. Carbon-based materials may include by way of non-limiting example, particles of KETCHEN™ black electrically-conductive carbon black, DENKA™ black electrically-conductive acetylene black, acetylene black, carbon black, and the like. Examples of a conductive polymer include polyaniline, polythiophene, polyacetylene, polypyrrole, and the like. In certain aspects, mixtures of conductive materials may be used.

An electrode may be made by mixing the electrode active material, such as lithium particles, into a slurry with a polymeric binder compound, a non-aqueous solvent, optionally a plasticizer, and optionally if necessary, electrically conductive particles. The slurry can be mixed or agitated, and then thinly applied to a substrate via a doctor blade. The substrate can be a removable substrate or alternatively a functional substrate, such as a current collector (such as a metallic grid or mesh layer) attached to one side of the electrode film. In one variation, heat or radiation can be applied to evaporate the solvent from the electrode film, leaving a solid residue. The electrode film may be further consolidated, where heat and pressure are applied to the film to sinter and calendar it. In other variations, the film may be air-dried at moderate temperature to form self-supporting films. If the substrate is removable, then it is removed from the electrode film that is then further laminated to a current collector. With either type of substrate, it may be necessary to extract or remove the remaining plasticizer prior to incorporation into the battery cell.

In other variations, a negative electrode 22 may be in the form of lithium metal, such as a lithium foil or lithium film. The lithium metal layer may be disposed on the negative electrode current collector 32.

In certain variations, pre-fabricated electrodes formed of electroactive material via the active material slurry casting described above can be directly coated via a vapor coating formation process to form a conformal inorganic-organic composite surface coating, as described further below. Thus, one or more exposed regions of the pre-fabricated negative electrodes comprising the electroactive material can be coated to minimize or prevent reaction of the electrode materials with components within the electrochemical cell to minimize or prevent lithium metal dendrite formation on the surfaces of negative electrode materials when incorporated into the electrochemical cell. In other variations, a plurality of particles comprising an electroactive material, like lithium metal, can be coated with an inorganic-organic composite surface coating. Then, the coated electroactive particles can be used in the active material slurry to form the negative electrode, as described above.

The negative electrode current collector 32 may be formed from copper or any other appropriate electrically conductive material known to those of skill in the art.

Each of the separator 26, the negative electrode 22, and the positive electrode 24 may include an electrolyte system 30, capable of conducting lithium ions between the negative electrode 22 and the positive electrode 24. In various aspects, the electrolyte system 30 may be a non-aqueous liquid electrolyte solution including a lithium salt and at least one additive compound dissolved in an organic solvent or a mixture of organic solvents.

A battery may thus be assembled in a laminated cell structure, comprising an anode layer, a cathode layer, and electrolyte/separator between the anode and cathode layers. The anode and cathode layers each comprise a current collector. A negative anode current collector may be a copper collector foil, which may be in the form of an open mesh grid or a thin film. The current collector can be connected to an external current collector tab. A protective bagging material covers the cell and prevents infiltration of air and moisture. Into this bag, an electrolyte is injected into the separator (and may also be imbibed into the positive and/or negative electrodes) suitable for lithium ion transport. In certain aspects, the laminated battery is further hermetically sealed prior to use.

Unlike conventional lithium-ion batteries, lithium metal batteries are not well-suited for the use of a single liquid or gel electrolyte. Thus, instead of a single liquid or gel electrolyte, two alternative types of electrolyte systems for lithium metal batteries have been tested: (1) an all-solid system; and (2) a solid-liquid system.

The all-solid system includes a solid-state electrolyte (SSE) disposed between a positive electrode and a negative electrode that includes lithium metal. The SSE serves as both an electrolyte and a separator, enabling transfer of lithium ions, while providing electrical insulation between the electrodes of different polarities. The SSE is formed from either a ceramic material (e.g., an oxide-based ceramic or a sulfide glass or glass-ceramic) or a polymeric material.

Ceramic SSEs have high ionic conductivity at room temperature. More specifically, oxide-based ceramics have a conductivity on the order of about 0.1-1 mS/cm at 23° C. Sulfide glasses and glass-ceramics have a conductivity on the order of about 0.1-10 mS/cm. Ceramic SSEs also have desirable mechanical properties (i.e., high shear modulus) for preventing the growth of dendrites on the negative electrode. However, the use of a ceramic SSE also has potential drawbacks. One is a high rigidity. It is difficult to maintain surface contact between a rigid electrolyte and the negative electrode as the surface of the negative electrode becomes uneven due to dendrite growth because the inflexibility of the electrolyte prevents it from conforming to the surface roughness of the negative electrode. The lack of conformity at the interface can lead to an undesirable increased resistance.

Polymeric SSEs are more compliant than ceramic SSEs. Thus, polymeric SSEs are capable of maintaining surface contact with the negative electrode as the surface of the negative electrode becomes rough due to growth of dendrites. However, polymeric SSEs have a low ionic conductivity at room temperature (e.g., less than 0.01 mS/cm). Furthermore, polymeric SSEs have insufficient mechanical properties (i.e., low shear modulus) to block dendrites from growing to reach the positive electrode. Thus, both ceramic and polymeric SSEs suffer from potential drawbacks that lead to a low working current density (i.e., lower power).

A solid-liquid system includes a positive electrode, a negative electrode including a lithium metal, and an electrolyte system disposed between the positive electrode and the negative electrode. The electrolyte system includes a liquid electrolyte component and a polymeric component (e.g., a polymer protection layer).

The liquid electrolyte component and the polymeric component may be distinct layers, or they may be blended. When the components are present as distinct layers, the liquid electrolyte may be disposed adjacent to the positive electrode and the polymeric component, which may include one or more layers, may be disposed between the liquid electrolyte and the negative electrode. When the components are blended, the resultant electrolyte system may have a blended gel or composite structure. As described above with respect to the all-solid polymeric SSE, such an interface with the lithium-metal negative electrode may exhibit poor mechanical properties that may fail to sufficiently block the growth of dendrites into the positive electrode.

In various aspects, the present disclosure provides a hybrid electrolyte system for a lithium metal battery. The hybrid electrolyte system includes a dendrite-blocking layer disposed between a first liquid electrolyte that is in contact with the cathode and an interface layer that is in contact with the anode. In certain aspects, the dendrite-blocking layer includes multiple distinct components, such as one or more ceramic SSEs and one or more polymeric SSEs. The multi-component dendrite-blocking layer combines desirable attributes of each of the components, so that it has a high ionic conductivity and shear modulus, while being compliant enough to maintain contact with the anode. In various aspects, the first liquid electrolyte and the interface layer each include electrolytes that are particularly suitable for the respective cathode and anode.

Figure 2:
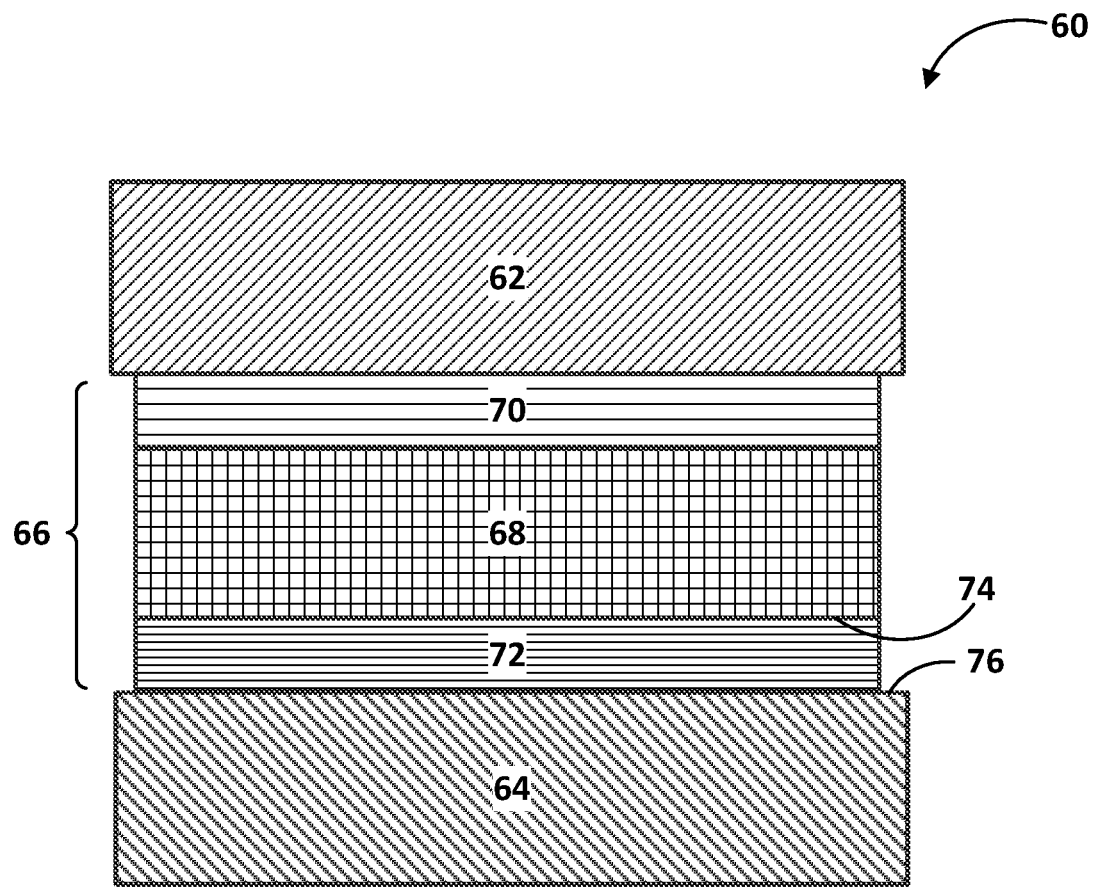
FIG. 2 is a schematic of an exemplary electrochemical cell having a hybrid electrolyte system according to certain aspects of the present disclosure.

Referring to FIG. 2, an example electrochemical cell 60 according to certain aspects of the present disclosure is shown. The electrochemical cell 60 includes a positive electrode (i.e., cathode) 62, a negative electrode (i.e., anode) 64, and an electrolyte system 66. In various aspects, the electrolyte system 66 also functions as a separator to provide a physical barrier between the positive and negative electrodes 62, 64. The electrolyte system 66 includes a dendrite-blocking layer 68, a first liquid electrolyte 70 disposed between the dendrite-blocking layer 68 and the positive electrode 62, and an interface layer 72 disposed between the dendrite-blocking layer 68 and the negative electrode 64.

The positive electrode 62 is similar to the positive electrode 24 of FIG. 1. Thus, the positive electrode 62 may include one or more transition metals as an electroactive material. By way of non-limiting example, the positive electrode 62 may be formed from lithium cobalt oxide ($LiCoO_2$) (LCO), lithium manganese oxide ($LiMn_2O_4$) (LMO), lithium nickel manganese spinel ($LiNi_{0.5}Mn_{1.5}O_4$) (LMNO), lithium nickel cobalt aluminum oxide ($LiNiCoAlO_2$) (NCA), lithium nickel cobalt manganese oxide ($LiNiCoMnO_2$) (NMC), and lithium iron phosphate ($LiFePO_4$) (LFP). In various aspects, the positive electrode 62 may include sulfur-based compounds. A sulfur-based compound may be selected from at least one of: elemental sulfur, $Li_2S_n$ (wherein n greater than or equal to 1), $Li_2S_n$ (wherein n greater than or equal to 1) dissolved in a catholyte, an organosulfur compound, and a carbon-sulfur polymer (($C_2S_x)_n$: wherein x=2.5, and n is 2 or greater). The positive electrode 62 may also include a binder and an electrically conductive material as described above.

The negative electrode 64 may be similar to the negative electrode 22 of FIG. 1. Thus, the negative electrode 64 may include a lithium-containing material, such as lithium particles or lithium foil. The negative electrode 64 may further include a binder and an electrically conductive material, as described above.

The dendrite-blocking layer 68 is disposed between the positive electrode 62 and the negative electrode 64. The dendrite-blocking layer 68 serves multiple purposes: (1) it acts as an electrolyte to transport lithium ions; (2) it is electrically insulating and can serve as a separator between electrodes of differing polarities (3) it provides a physical barrier to separate the positive and negative electrodes 62, 64 and to block dendrite growth on the negative electrode 64 to the positive electrode 62. To meet the above functional requirements, the dendrite-blocking layer 68 is sufficiently ionically-conductive to function as an electrolyte and sufficiently resistive and insulating, while providing mechanical properties to inhibit the growth of dendrites. More specifically, the dendrite-blocking layer optionally has an ionic conductivity of greater than 0.01 mS/cm. To sufficiently block the growth of dendrites on the negative electrode 64, in certain variations, the dendrite-blocking layer 68 may have a shear modulus of greater than or equal to about 7.5 GPa (e.g., 7.56 GPa) at room temperature, optionally greater than or equal to about 8 GPa, optionally greater than or equal to about 9 GPa, and optionally greater than or equal to about 10 GPa.

The dendrite-blocking layer 68 may include one or more components. In various aspects, the dendrite-blocking layer 68 may include a single component. Exemplary single-component dendrite-blocking layers 68 may include: pure oxide-based ceramics, phosphates (e.g., ($Li_{1.3}Al_{0.3}Ti_{1.7}(PO_4)_3$) (LATP)), perovskites ((e.g., $Li_{0.67-x}La_{3x}TiO_3$)

(LLTO)), and garnets (e.g., ($Li_7La_3Zr_2O_{12}$) (LLZO)). However, any materials that meet the requirements for ionic conductivity and shear modulus may be used to form the dendrite-blocking layer 68 and are such materials are therefore contemplated within the scope of the present disclosure.

In various aspects, the dendrite-blocking layer 68 is a multi-component phase. The multi-component dendrite-blocking layer 68 may include ceramic, polymeric, inorganic, and organic materials. In certain aspects, a solid dendrite-blocking layer 68 that is ionically conducting, electrically insulating, and has a shear modulus of greater than or equal to about 7.5 GPa at 23° C. may include a first component and a distinct second component. The first component may be a ceramic material, such as a solid-state ceramic, glass, or glass ceramic and the second component may be a polymer. Suitable solid phase materials may include solid-state ceramic, glass, or glass-ceramic electrolytes such as ceramic oxides and sulfide glasses or glass-ceramics. Non-limiting examples of ceramic oxides include: phosphates (e.g., lithium aluminum titanium phosphate ($Li_{1.3}Al_{0.3}Ti_{1.7}(PO_4)_3$) (LATP)), perovskites (e.g., lithium lanthanum titanate ($Li_{0.67-x}La_{3x}TiO_3$) (LLTO)), and garnets (e.g., lithium lanthanum zirconium oxide ($Li_7La_3Zr_2O_{12}$) (LLZO)). A non-limiting example of a sulfide glass is lithium phosphorous sulfide ($70Li_2S-30P_2S_5$) (LPS). A non-limiting example of a sulfide glass-ceramic is lithium phosphorus sulfide ($70Li_2S-30P_2S_5$) (c-LPS) which has been devitrified to form the ionically conductive $Li_7P_3S_{11}$ crystalline phase. Polymeric materials may include solid-state polymeric electrolytes such as polyethylene oxide (PEO), by way of non-limiting example. Other inorganic materials may include anti-perovskites, complex hydrides, oxide glasses, oxysulfide glasses, and LiPON, by way of non-limiting examples. Other organic materials may include poly(methyl methacrylate) (($C_5O_2H_8)_n$) (PMMA), polyacrylonitrile (($C_3H_3N)_n$) (PAN), polyvinylidene fluoride (($C_2H_2F_2)_n$) (PVDF), and gel electrolytes (i.e., polymers plasticized with solvent) by way of non-limiting example.

The multi-component dendrite-blocking layer 68 may be in the form of a composite, laminate, or any other engineered structure that results in a material having sufficient ionic conductivity and mechanical properties. One such composite includes a sulfide-based SSE component, an oxide-based SSE component, and a polymer linker component. A laminate structure includes alternating layers of two or more materials, for example, a sulfide-based SSE layer and a polymer layer. The above examples are non-limiting and the multi-component dendrite-blocking layer 68 according to certain aspects of the present disclosure may include other combinations of materials that result in a dendrite-blocking layer 68 having the requisite ionic conductivity and shear modulus.

By using a multi-component structure, the solid dendrite-blocking layer 68 combines attributes of each of the materials forming its distinct components. Thus, a solid dendrite-blocking layer 68 having both polymer and ceramic includes the beneficial rigidity and ionic conductivity of a ceramic SSE while also having the desirable compliance of a polymeric SSE. These properties enable the dendrite-blocking layer 68 to prevent dendritic shorts at high current densities (i.e., greater than or equal to 3 $mA \cdot cm^{-2}$) and minimize the resistance of the dendrite-blocking layer 68.

The first liquid electrolyte 70 is disposed between the dendrite-blocking layer 68 and the positive electrode 62. The first liquid electrolyte 70 may include one or more lithium salts and a solvent, which may be an organic solvent, or a mixture of organic solvents. In one variation, the one or more lithium salts may be selected from the group consisting of: lithium hexafluorophosphate ($LiPF_6$); lithium perchlorate ($LiClO_4$); lithium tetrachloroaluminate ($LiAlCl_4$); lithium iodide (LiI); lithium bromide (LiBr); lithium thiocyanate (LiSCN); lithium tetrafluoroborate ($LiBF_4$); lithium tetraphenylborate ($LiB(C_6H_5)_4$); lithium hexafluoroarsenate ($LiAsF_6$); lithium trifluoromethanesulfonate ($LiCF_3SO_3$); lithium fluorosulfonylimide $LiN(FSO_2)_2$ (LIFSI); bis(trifluoromethane)sulfonimide lithium ($LiN(CF_3SO_2)_2$) (LiTFSI); lithium bis-(oxalate)borate $LiB(C_2O_4)_2$ (LiBOB); lithium difluoro-(oxalate)borate $LiBF_2(C_2O_4)$ (LiODFB); $LiPF_4(C_2O_4)$ (LiFOP); $LiNO_3$; and combinations thereof.

In one variation, the one or more solvents may be selected from the group consisting of: cyclic carbonates (e.g., ethylene carbonate (EC), propylene carbonate (PC), butylene carbonate (BC), fluoroethylene carbonate (FEC)); acyclic (i.e., linear) carbonates (e.g., dimethyl carbonate (DMC), diethyl carbonate (DEC), ethylmethylcarbonate (EMC)); aliphatic carboxylic esters (e.g., methyl formate, methyl acetate, methyl propionate); γ-lactones (e.g., γ-butyrolactone, γ-valerolactone); chain structure ethers (e.g., 1,2-dimethoxyethane, 1-2-diethoxyethane, ethoxymethoxyethane); cyclic ethers (e.g., tetrahydrofuran, 2-methyltetrahydrofuran, 1,3-dioxolane); and combinations thereof.

When the dendrite-blocking layer 68 is sufficiently impermeable (i.e., pores of the dendrite-blocking layer are not interconnecting), the first liquid electrolyte 70 may selected to be particularly compatible with the material forming the positive electrode 62 (e.g., a metal oxide-based positive electrode material). Thus, in certain variations, the first liquid electrolyte 70 may be carbonate based (e.g., EC, PC, BC, FEC, DMC, DEC, EMC) for optimal compatibility with the positive electrode 62.

The interface layer 72 is disposed between the dendrite-blocking layer 68 and the negative electrode 64. The interface layer 72 serves two purposes: (1) it reduces resistance between the dendrite-blocking layer 68 and the negative electrode 64; and (2) it eliminates or reduces unwanted chemical reactions between the dendrite-blocking layer 68 and the negative electrode 64.

Absent the interface layer 72, a first surface 74 of the dendrite-blocking layer and a second surface 76 of the negative electrode 64 would be in solid-to-solid contact. Thus, as discussed above in the context of all-solid lithium metal batteries, resistance between the dendrite-blocking layer 68 and the negative electrode 64 may increase throughout the life of the battery. The increased resistance is due to the formation of dendrites on the surface 76 of the negative electrode 64, which creates a rough surface an imperfect contact between the surfaces 74, 76.

Unwanted side reactions between the dendrite-blocking layer 68 and the negative electrode 64 may occur when the interface layer 72 is not present, depending on the composition of the dendrite-blocking layer 68 and the negative electrode 64. The side reactions can compromise coulombic efficiency and cycling lifetime of the cell 60 and are therefore undesirable. Thus, the presence of the interface layer 72 can reduce or eliminate side reactions between the dendrite-blocking layer 68 and the negative electrode 64, thereby improving the performance of the cell 60.

The interface layer 72 may include liquid electrolytes, gel polymer electrolytes, or solid-state electrolytes. In various embodiments, the interface layer 72 may include more than one of second liquid electrolytes, gel polymer electrolytes, and solid-state electrolytes in a mixed or layered format. In some embodiments, the interface layer may include a membrane similar to the porous separator 26 of FIG. 1 in addition to the liquid electrolyte, gel polymer electrolyte, and solid-state electrolyte. When the interface layer 72 includes a second liquid electrolyte, the second liquid electrolyte of the interface layer 72 may have the same composition as the first liquid electrolyte 70 or a different composition than the first liquid electrolyte 70. Thus, a second liquid electrolyte of the interface layer may include one or more lithium salts and one or more organic solvents.

In one variation, the one or more lithium salts may be selected from the group consisting of: lithium hexafluorophosphate ($LiPF_6$); lithium perchlorate ($LiClO_4$); lithium tetrachloroaluminate ($LiAlCl_4$); lithium iodide (LiI); lithium bromide (LiBr); lithium thiocyanate (LiSCN); lithium tetrafluoroborate ($LiBF_4$); lithium tetraphenylborate ($LiB(C_6H_5)_4$); lithium hexafluoroarsenate ($LiAsF_6$); lithium trifluoromethanesulfonate ($LiCF_3SO_3$); lithium fluorosulfonylimide $LiN(FSO_2)_2$ (LIFSI); bis(trifluoromethane)sulfonimide lithium ($LiN(CF_3SO_2)_2$) (LiTFSI); lithium bis-(oxalate)borate $LiB(C_2O_4)_2$ (LiBOB); lithium difluoro-(oxalate)borate $LiBF_2(C_2O_4)$ (LiODFB); $LiPF_4(C_2O_4)$ (LiFOP); $LiNO_3$; and combinations thereof.

In one variation, the one or more solvents may be selected from the group consisting of: cyclic carbonates (e.g., ethylene carbonate (EC), propylene carbonate (PC), butylene carbonate (BC), fluoroethylene carbonate (FEC)); acyclic (i.e., linear) carbonates (e.g., dimethyl carbonate (DMC), diethyl carbonate (DEC), ethylmethylcarbonate (EMC)); aliphatic carboxylic esters (e.g., methyl formate, methyl acetate, methyl propionate); γ-lactones (e.g., γ-butyrolactone, γ-valerolactone); chain structure ethers (e.g., 1,2-dimethoxyethane, 1-2-diethoxyethane, ethoxymethoxyethane); cyclic ethers (e.g., tetrahydrofuran, 2-methyltetrahydrofuran, 1,3-dioxolane); and combinations thereof.

When the dendrite-blocking layer 68 is sufficiently impermeable to the second electrolyte in the interface layer 72, the second liquid electrolyte of the interface layer 72 may selected to be particularly compatible with the lithium metal-based negative electrode 64. Thus, in certain variations, the liquid electrolyte of the interface layer 72 may be ether-based based (e.g., 1,2-dimethoxyethane, 1-2-diethoxyethane, ethoxymethoxyethane, tetrahydrofuran, 2-methyltetrahydrofuran, 1,3-dioxolane) for optimal compatibility with the negative electrode 64.

The interface layer 72 may alternatively include a gel polymer electrolyte. A gel polymer electrolyte is formed by plasticizing a polymer electrolyte with a suitable solvent (e.g., carbonate- or ether-based solvents). Polymer electrolytes may include polyvinylidene difluoride (PVDF), polymethylmethacrylate (PMMA), polyalkylene oxide (PAO), such as polyethyleneoxide (PEO) or polypropylene oxide (PPO), copolymers, and combinations thereof, by way of non-limiting example.

The interface layer 72 may alternately include a solid-state electrolyte. The solid state electrolyte may be ceramic or polymeric. In some variations, the interface layer 72 may be formed from a solid-state electrolyte having a multi-component structure (e.g., composite or laminate) similar to the multi-component structures described above with respect to the dendrite-blocking layer 68. Although another solid-state electrolyte material can be used in the interface layer 72, the interface layer 72 preferably has a better compliancy as compared to the dendrite-blocking layer 68 to promote better contact between the dendrite-blocking layer 68 and the negative electrode 64.

Figure 3:
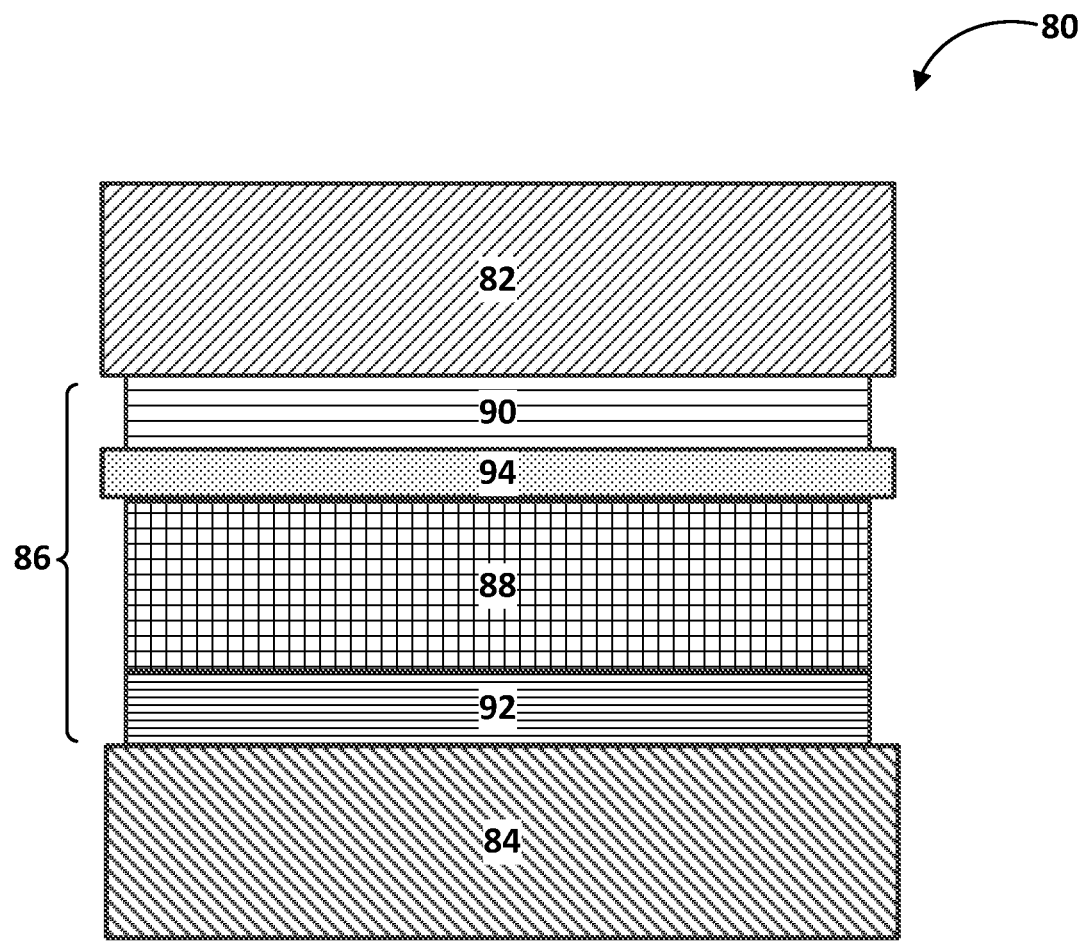
FIG. 3 is a schematic of another exemplary electrochemical cell having a hybrid electrolyte system, including a polymeric membrane, according to certain aspects of the present disclosure.

With reference to FIG. 3, another example electrochemical cell 80 according to certain aspects of the present disclosure is shown. The electrochemical cell 80 includes a positive electrode (i.e., cathode) 82, a negative electrode (i.e., anode) 84, and an electrolyte system 86. The positive electrode 82 may be metal oxide-based and may be similar to the positive electrode 62 of FIG. 2. The negative electrode 84 may be lithium metal-based and may be similar to the negative electrode 64 of FIG. 2. The electrolyte system 86 includes a dendrite-blocking layer 88, a first liquid electrolyte 90, an interface layer 92, and a polymeric membrane 94, which may serve as a separator structure as described further below. The dendrite-blocking layer 88, first liquid electrolyte 90, and interface layer 92 may be similar to the dendrite-blocking layer 68, first liquid electrolyte 70, and interface layer 72 of the electrochemical cell 60 of FIG. 2.

The use of the polymeric membrane 94 is particularly advantageous in electrolyte systems 86 where the dendrite-blocking layer 88 is not oxidatively stable versus the positive electrode 82. The positive electrode 82 has an operational upper voltage limit. The dendrite-blocking layer 88 is oxidatively stable when it will not decompose at voltages less than or equal to the operational upper voltage limit of the positive electrode 82. Conversely, the dendrite-blocking layer 88 is not oxidatively stable when it will decompose at voltages less than or equal to the operational upper voltage limit of the positive electrode 82.

In one variation, the positive electrode 82 is formed from NMC, which has an operational upper voltage limit of 4.3 volts. PEO and LPS are non-limiting examples of materials that are not oxidatively stable at less than or equal to 4.3 volts. Thus, when the dendrite-blocking layer 88 is formed from PEO or LPS, the electrochemical cell 80 would preferably further include the polymeric membrane 94. LLTO, LLZO, and LATP are non-limiting examples of materials that are oxidatively stable at less than or equal to 4.3 volts. Thus, when the dendrite-blocking layer 88 is formed from LLTO, LLZO, or LATP, the electrochemical cell 80 may exclude the polymeric membrane 94 (i.e., the electrochemical cell 80 may be similar to the electrochemical cell 60 of FIG. 2).

The polymeric membrane 94 may be similar to the porous separator 26 of FIG. 1. Thus, the polymeric membrane 94 may include, in certain instances, a microporous polymeric separator including a polyolefin, by way of non-limiting example. The polyolefin may be a homopolymer or a heteropolymer, which may be either linear or branched. If a heteropolymer is derived from two monomer constituents, the polyolefin may assume any copolymer chain arrangement, including those of a block copolymer or a random copolymer. Similarly, if the polyolefin is a heteropolymer derived from more than two monomer constituents, it may likewise be a block copolymer or a random copolymer. In certain aspects, the polyolefin may be polyethylene (PE), polypropylene (PP), or a blend of PE and PP, or multi-layered structured porous films of PE and/or PP.

When the polymeric membrane 94 is a microporous polymeric separator, it may be a single layer or a multi-layer laminate, which may be fabricated from either a dry or wet process. For example, in one embodiment, a single layer of the polyolefin may form the entire polymeric membrane 94. In other aspects, polymeric membrane 94 may be a fibrous membrane having an abundance of pores extending between the opposing surfaces and may have a thickness of less than a millimeter, for example. As another example, however, multiple discrete layers of similar or dissimilar polyolefins may be assembled to form the polymeric membrane 94.

Furthermore, the polymeric membrane may be mixed with a ceramic material or its surface may be coated in a ceramic material. For example, a ceramic coating may include alumina ($Al_2O_3$), silicon dioxide ($SiO_2$), or combinations thereof.

Embodiments of the present technology are further illustrated through the following non-limiting examples.

Exemplary electrochemical cells were prepared according to certain aspects of the present disclosure.

Example 1—Lithium Metal Anode and NMC Cathode

Figure 4:
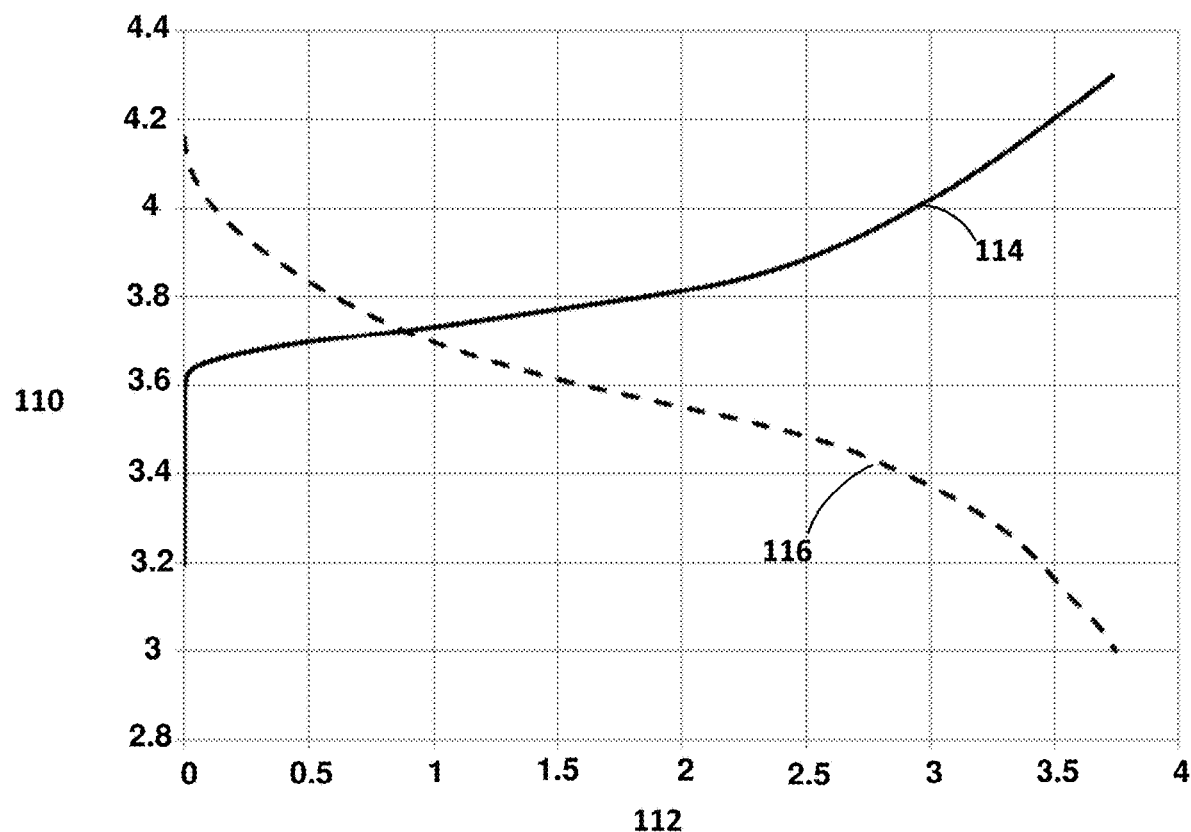
FIG. 4 is a graphical representation of first cycle charge and discharge curves of an exemplary electrochemical cell according to certain aspects of the present disclosure.

An electrochemical cell according to certain aspects of the present disclosure includes a lithium metal-based anode and an NMC-based cathode. An electrolyte system of the electrochemical cell includes a dendrite-blocking layer comprising aramid fiber-(KEVLAR™) reinforced sulfide glass ($70Li_2S-30P_2S_5$). Both the liquid electrolyte and the interface layer include a carbonate-based electrolyte. More specifically, the carbonate-based electrolyte includes a carbonate solvent with 1 M $LiPF_6$ dissolved in fluoroethylene carbonate:dimethyl carbonate (FED:DMC (1:4 v:v)). In addition to the carbonate-based electrolyte, the interface layer includes a CELGARD polypropylene separator. FIG. 4 shows voltage (volts) on the y-axis 110 and capacity (mAh/$cm^2$) on the x-axis 112. The first cycle charge curve is shown at 114 and the first cycle discharge curve is shown at 116. Tests were run at a voltage limit of 3.0-4.3 V, a charge current of 0.25 mA/$cm^2$, and a discharge current of 0.6 mA/$cm^2$.

Example 2—Lithium Metal Anode and Sulfur Cathode

Figure 5:
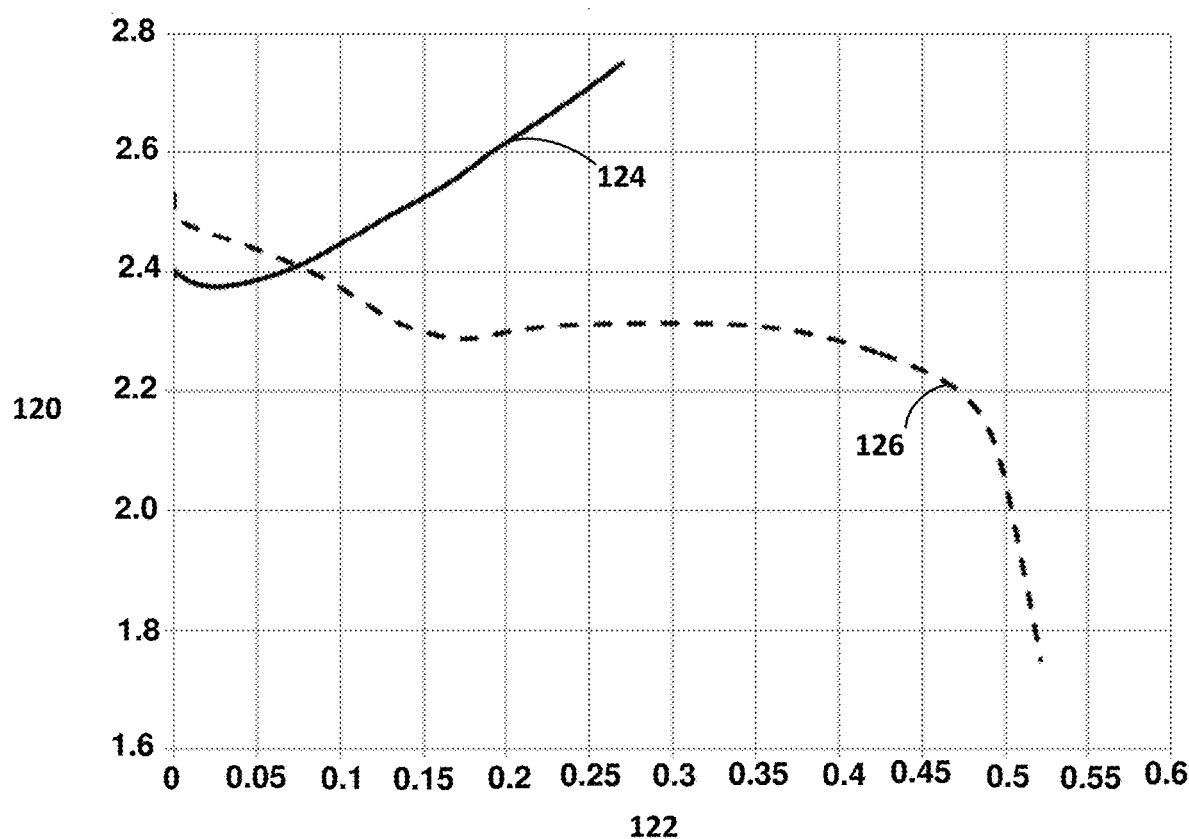
FIG. 5 is a graphical representation of first cycle charge and discharge curves of another exemplary electrochemical cell according to certain aspects of the present disclosure.

An electrochemical cell according to certain aspects of the present disclosure includes a lithium metal-based anode and a sulfur-based cathode. An electrolyte system of the electrochemical cell includes a dendrite-blocking layer comprising aramid fiber-(KEVLAR™) reinforced sulfide glass ($70Li_2S-30P_2S_5$). Both the liquid electrolyte and the interface layer include an ether-based electrolyte. More specifically, the ether-based electrolyte includes 1M LiTFSI dissolved in dimethoxyethane:1, 3-dioxolane (DME:DIOX (1:1 v:v)) and 2% $LiNO_3$. In addition to the ether-based electrolyte, the interface layer includes also includes a CELGARD polypropylene separator. FIG. 5 shows voltage (volts) on the y-axis 120 and capacity (mAh/$cm^2$) on the x-axis 122. The first cycle charge curve is shown at 124 and the first cycle discharge curve is shown at 126. Tests were run at a voltage limit of 1.75-2.75 V, a charge current of 0.165 mA/$cm^2$, and a discharge current of 0.165 mA/$cm^2$.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An electrolyte system for an electrochemical cell, the electrolyte system comprising:
a first liquid electrolyte comprising a non-aqueous organic solvent and configured to interface with a positive electrode;
a solid dendrite-blocking layer that is ionically conducting and electrically insulating and comprises a first component and a distinct second component, the dendrite-blocking layer having a shear modulus of greater than or equal to about 7.5 GPa at 23° C., the first component comprising a solid-state ceramic, glass, or glass-ceramic and the second component comprising a solid-state polymer, the solid-state polymer comprising polyethylene oxide; and
an interface layer configured to interface with a negative electrode comprising lithium metal on a first side of the interface layer and the dendrite-blocking layer on a second opposite side of the interface layer, the interface layer comprising a second liquid electrolyte, a gel polymer electrolyte, or a solid-state electrolyte, wherein the dendrite-blocking layer is disposed between the first liquid electrolyte and the interface layer.

2. The electrolyte system of claim 1, the interface layer comprises the gel polymer electrolyte.

3. The electrolyte system of claim 1, wherein the interface layer comprises the solid-state electrolyte.

4. The electrolyte system of claim 1, further comprising a polymeric membrane disposed between the first liquid electrolyte and the dendrite-blocking layer.

5. The electrolyte system of claim 1, wherein the dendrite-blocking layer has a composite structure comprising the first component and the second component.

6. The electrolyte system of claim 1, wherein the dendrite-blocking layer is impermeable to the first liquid electrolyte.

7. The electrolyte system of claim 1, wherein the dendrite-blocking layer has a laminate structure including one or more layers of the first component and one or more layers of the second component.

8. The electrolyte system of claim 1, wherein the solid-state ceramic, glass, or glass-ceramic is selected from the group consisting of: lithium aluminum titanium phosphate, lithium lanthanum titanate, lithium lanthanum zirconium oxide, lithium phosphorous sulfide, and combinations thereof.

9. The electrolyte system of claim 1, wherein the first component comprises the glass.

10. The electrolyte system of claim 9, wherein the glass comprises a sulfide glass.

11. The electrolyte system of claim 10, wherein the sulfide glass comprises lithium phosphorous sulfide.

12. An electrochemical cell comprising:
a positive electrode comprising a metal oxide;
a negative electrode comprising lithium; and
an electrolyte system comprising a solid dendrite-blocking layer that is electrically insulating, ionically-conductive, and has a shear modulus of greater than or equal to about 7.5 GPa at 23° C., the dendrite-blocking layer being disposed between the positive electrode and the negative electrode; the dendrite-blocking layer comprising a first component comprising a solid-state ceramic, glass, or glass-ceramic and a second component comprising a solid-state polymer comprising polyethylene oxide, a first liquid electrolyte disposed between the positive electrode and the dendrite-blocking layer, the first liquid electrolyte comprising a non-aqueous organic solvent; and an interface layer disposed between the negative electrode and the dendrite-blocking layer and configured to interface with the negative electrode and the dendrite-blocking layer, the interface layer comprising a second liquid electrolyte, a gel polymer electrolyte, or a solid-state electrolyte.

13. The electrochemical cell of claim 12, wherein the interface layer comprises an ether-based electrolyte.

14. The electrochemical cell of claim 12, wherein the first liquid electrolyte is in direct contact with the dendrite-blocking layer.

15. The electrochemical cell of claim 12, wherein the dendrite-blocking layer has a composite structure comprising the first component and the second component.

16. The electrochemical cell of claim 12, wherein the dendrite-blocking layer has a laminate structure including one or more layers of the first component and one or more layers of the second component.

17. The electrochemical cell of claim 12, wherein the electrolyte system further comprises a polymeric membrane disposed between the first liquid electrolyte and the dendrite-blocking layer.

18. The electrochemical cell of claim 12, wherein the metal oxide is selected from the group consisting of: lithium cobalt oxide, lithium manganese oxide, lithium nickel manganese spinel, lithium nickel cobalt aluminum oxide, lithium nickel cobalt manganese oxide, lithium iron phosphate, and combinations thereof.

19. The electrochemical cell of claim 12, wherein the solid-state ceramic, glass, or glass ceramic is selected from the group consisting of: lithium aluminum titanium phosphate, lithium lanthanum titanate, lithium lanthanum zirconium oxide, lithium phosphorous sulfide, and combinations thereof.

20. The electrochemical cell of claim 12, wherein the non-aqueous organic solvent is selected from the group consisting of: ethylene carbonate (EC), propylene carbonate (PC), butylene carbonate (BC), fluoroethylene carbonate (FEC), dimethyl carbonate (DMC), diethyl carbonate (DEC), ethylmethylcarbonate (EMC), and combinations thereof.

* * * * *